US010398399B2

(12) United States Patent
Madabhushi et al.

(10) Patent No.: US 10,398,399 B2
(45) Date of Patent: *Sep. 3, 2019

(54) DECISION SUPPORT FOR DISEASE CHARACTERIZATION AND TREATMENT RESPONSE WITH DISEASE AND PERI-DISEASE RADIOMICS

(71) Applicant: Case Western Reserve University, Cleveland, OH (US)

(72) Inventors: Anant Madabhushi, Shaker Heights, OH (US); Mahdi Orooji, Cleveland, OH (US); Mirabela Rusu, Cleveland, OH (US); Philip Linden, Pepper Pike, OH (US); Robert Gilkeson, Cleveland Heights, OH (US); Nathaniel Mason Braman, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/937,105

(22) Filed: Mar. 27, 2018

(65) Prior Publication Data

US 2018/0214111 A1    Aug. 2, 2018

Related U.S. Application Data

(63) Continuation of application No. 15/226,124, filed on Aug. 2, 2016, now Pat. No. 10,004,471.
(Continued)

(51) Int. Cl.
*A61B 6/00* (2006.01)
*G06T 11/00* (2006.01)
(Continued)

(52) U.S. Cl.
CPC ............ *A61B 6/5217* (2013.01); *A61B 5/055* (2013.01); *A61B 5/08* (2013.01); *A61B 5/4312* (2013.01);
(Continued)

(58) Field of Classification Search
CPC ......... G06T 2207/30096; G06T 7/0012; G06T 7/62; G06T 11/008; G06T 17/10;
(Continued)

(56) References Cited

U.S. PATENT DOCUMENTS 9,092,691 B1 * 7/2015 Beaumont ............. G06T 7/0014
2003/0095692 A1 * 5/2003 Mundy .................... A61B 6/00
382/128
(Continued)

OTHER PUBLICATIONS

Notice of Allowance dated May 2, 2018 for U.S. Appl. No. 15/226,148.
(Continued)

*Primary Examiner* — Aklilu K Woldemariam
(74) *Attorney, Agent, or Firm* — Eschweiler & Potashnik, LLC

(57) ABSTRACT

Methods, apparatus, and other embodiments associated with classifying a region of tissue using textural analysis are described. One example apparatus includes an image acquisition logic that acquires an image of a region of tissue demonstrating cancerous pathology, a delineation logic that distinguishes nodule tissue within the image from the background of the image, a perinodular zone logic that defines a perinodular zone based on the nodule, a feature extraction logic that extracts a set of features from the image, a probability logic that computes a probability that the nodule is benign or that the nodule will respond to a treatment, and a classification logic that classifies the nodule tissue based, at least in part, on the set of features or the probability. A
(Continued)

prognosis or treatment plan may be provided based on the classification of the image.

18 Claims, 8 Drawing Sheets

Related U.S. Application Data

(60) Provisional application No. 62/201,837, filed on Aug. 6, 2015.

(51) Int. Cl.

| | | |
|---|---|---|
| G06K 9/46 | (2006.01) | |
| G06K 9/00 | (2006.01) | |
| A61B 6/03 | (2006.01) | |
| A61B 5/08 | (2006.01) | |
| A61B 5/055 | (2006.01) | |
| A61B 5/00 | (2006.01) | |
| A61B 10/00 | (2006.01) | |
| G01R 33/56 | (2006.01) | |
| G06K 9/62 | (2006.01) | |
| G06T 7/00 | (2017.01) | |
| G06T 7/40 | (2017.01) | |
| G06T 7/11 | (2017.01) | |
| G06T 7/136 | (2017.01) | |
| G06T 7/62 | (2017.01) | |
| A61B 34/10 | (2016.01) | |
| A61B 6/12 | (2006.01) | |

(52) U.S. Cl.
CPC ............ *A61B 5/7267* (2013.01); *A61B 6/032* (2013.01); *A61B 10/0041* (2013.01); *G01R 33/5601* (2013.01); *G06K 9/00147* (2013.01); *G06K 9/46* (2013.01); *G06K 9/4604* (2013.01); *G06K 9/6267* (2013.01); *G06T 7/0012* (2013.01); *G06T 7/11* (2017.01); *G06T 7/136* (2017.01); *G06T 7/40* (2013.01); *G06T 7/62* (2017.01); *G06T 11/003* (2013.01); *G06T 11/008* (2013.01); *A61B 6/12* (2013.01); *A61B 2034/105* (2016.02); *G01R 33/5608* (2013.01); *G06K 9/00* (2013.01); *G06K 9/6269* (2013.01); *G06T 2207/10081* (2013.01); *G06T 2207/10096* (2013.01); *G06T 2207/20081* (2013.01); *G06T 2207/30064* (2013.01); *G06T 2207/30068* (2013.01); *G06T 2207/30101* (2013.01); *G06T 2211/404* (2013.01)

(58) Field of Classification Search
CPC ....... G06T 2200/04; G06T 2207/10072; G06T 2207/10081; G06T 2207/30101; G06T 5/002; G06T 5/005; G06T 2207/30064; G06T 5/30; G06T 7/11; G06T 7/155; G06T 2207/30061; G06T 2207/10116; G06T 2207/20004; G06T 7/20; G06T 7/60; G06T 7/74; G06T 5/02; G06T 15/08; G06T 2207/10028; G06T 11/003; G06T 2207/20016; G06T 2207/30068; G06T 2207/20081; G06T 2211/404; A61B 5/08; A61B 6/032; A61B 5/055; A61B 6/12; A61B 6/50; A61B 5/413; A61B 5/415; A61B 5/417; A61B 5/418; A61B 6/508; A61B 8/08; A61B 8/485; A61B 2034/105; A61B 6/5217; A61B 10/0041; A61B 5/4312; A61B 5/7267; A61B 5/4504; A61B 17/12031; A61B 17/12104; A61B 17/00234; A61B 17/12022; A61B 17/12131; A61B 17/1214; A61B 17/12145; A61B 17/1215; A61B 17/12172; A61B 1/018; A61B 1/04; A61B 5/0051; A61B 5/0053; A61B 5/015; A61B 8/085; A61B 10/0275; A61B 17/2251; A61B 17/225; A61B 17/2256; A61B 17/2258; A61B 18/12; A61B 2017/00026; A61B 2017/00061; G06K 9/00147; G06K 9/4604; G06K 9/00; G06K 9/46; G06K 9/6267; G06K 9/626; G01R 33/5601; G01R 33/5608
USPC ................ 382/128, 129, 130, 131, 132, 154
See application file for complete search history.

(56) References Cited

U.S. PATENT DOCUMENTS

| | | | | |
|---|---|---|---|---|
| 2004/0252870 | A1* | 12/2004 | Reeves ................ | G06T 7/0012 382/128 |
| 2005/0207630 | A1* | 9/2005 | Chan ...................... | A61B 6/466 382/131 |
| 2007/0081712 | A1* | 4/2007 | Huang ...................... | G06T 7/33 382/128 |
| 2008/0002870 | A1* | 1/2008 | Farag .................... | G06K 9/0014 382/128 |
| 2008/0205717 | A1* | 8/2008 | Reeves ................ | G06T 7/0012 382/128 |
| 2009/0005693 | A1* | 1/2009 | Brauner ................ | A61B 6/508 600/481 |
| 2010/0111386 | A1* | 5/2010 | El-Baz .................. | G06T 7/0016 382/128 |
| 2010/0323903 | A1* | 12/2010 | Rosenwald .......... | C12Q 1/6886 506/7 |
| 2012/0150048 | A1* | 6/2012 | Kang ..................... | A61B 6/508 600/481 |
| 2013/0217956 | A1* | 8/2013 | Thompson ........ | A61B 17/12022 600/37 |
| 2013/0225662 | A1* | 8/2013 | Kennedy .............. | C12Q 1/6886 514/44 R |
| 2013/0259345 | A1* | 10/2013 | El-Baz .................. | G06T 7/0012 382/131 |
| 2016/0110632 | A1* | 4/2016 | Kiraly .................... | G06K 9/66 382/128 |
| 2016/0155225 | A1* | 6/2016 | Madabhushi ......... | G06T 7/0012 382/131 |
| 2017/0039737 | A1* | 2/2017 | Madabhushi ........ | A61B 5/7267 |

OTHER PUBLICATIONS

Fraioli, et al. "CAD (Computed-Aided Detection) and CADx (Computer Aided Diagnosis) Systems in Identifying and Characterising Lung Nodules on Chest CT: Overview of Research, Developments and New Prospects." Radiol Med (2010) 115:385-402, published Jan. 15, 2010.

Awai, et al. "Pulmonary Nodules: Estimation of Malignancy at Thin-Section Helical CT—Effect of Computer-aided Diagnosis on Performance of Radiologists." Radiology: vol. 239: No. 1, Apr. 2006.

Ko, et al. "Lung Adenocarcinoma: Correlation of Quantitative CT Findings with Pathologic Findings." Radiology: vol. 280: No. 3, Sep. 2016.

Aoyama, et al. "Computerized Scheme for Determination of the Likelihood Measure of Malignancy for Pulmonary Nodules on Low-Dose CT Images." Med. Phys. 30 (3), Mar. 2003.

U.S. Appl. No. 15/226,148, filed Aug. 2, 2016.

Non-Final Office Action dated Oct. 30, 2017 for U.S. Appl. No. 15/226,148.

Non-Final Office Action dated Oct. 30, 2017 for U.S. Appl. No. 15/226,124.

Notice of Allowance dated Oct. 30, 2017 for U.S. Appl. No. 15/226,124.

(56) References Cited

OTHER PUBLICATIONS

Non Final Office Action dated Feb. 27, 2019 for U.S. Appl. No. 16/043,498.

* cited by examiner

DECISION SUPPORT FOR DISEASE CHARACTERIZATION AND TREATMENT RESPONSE WITH DISEASE AND PERI-DISEASE RADIOMICS

CROSS REFERENCE TO RELATED APPLICATIONS

This application is a Continuation of U.S. application Ser. No. 15/226,124 filed on Aug. 2, 2016, which claims priority to U.S. Provisional Application No. 62/201,837 filed on Aug. 6, 2015. The contents of the above-referenced matters are hereby incorporated by reference in their entirety.

BACKGROUND

Variations of nodule invasiveness and morphology relate to prognosis and patient outcomes. One approach for diagnosing disease is histopathological examination of biopsy tissue. The examination may produce a diagnostic profile based on attributes including cell morphology, cytoplasmic changes, cell density, or cell distribution. Visual characterization of tumor morphology is, however, time consuming, and expensive. Visual characterization is also subjective and thus suffers from inter-rater and intra-rater variability. Conventional visual characterization of nodule morphology by a human pathologist may therefore be less than optimal in clinical situations where timely and accurate classification can affect patient outcomes.

Computed tomography (CT) is frequently used to image nodules. For example, chest CT imagery may be used to detect and diagnose non-small cell lung cancer. However, conventional approaches to analyzing chest CT imagery have been challenged when attempting to distinguish a benign granuloma (Gr) from malignant adenocarcinoma (AC). For example, conventional CT-based approaches may find it difficult, if even possible at all, to reliably discriminate nodules caused by benign fungal infections from non-small cell lung cancer nodules. Histoplasmosis is a common endemic fungal infection in the United States. Granulomas secondary to histoplasmosis infection may appear identical to malignant lung nodules in CT imagery.

Other cancer types pose challenges when determining treatments or predicting response to treatment. Magnetic resonance imaging (MRI) is a common medical imaging modality for preparing or analyzing neo-adjuvant chemotherapy (NAC) for breast cancer. Administered prior to surgery, NAC can reduce the extent of tumor burden and increase a patient's surgical options. The ideal outcome of NAC is pathological complete response (pCR), which is the complete disappearance of residual invasive tumor cells within excised breast tissue. However, less than 25% of breast cancer patients who undergo NAC will achieve pCR.

Since radiologists may be challenged to reliably distinguish Gr secondary to benign fungal infections from AC in situ using conventional CT approaches in clinically optimal or relevant time frames, invasive procedures may be performed that ultimately result in a negative diagnosis. For example, many patients with benign granulomas are subjected to unnecessary surgical resections and biopsies. These invasive procedures take time, cost money, and put a patient at additional risk. As the number of routine chest CT scans increases with the wide-spread adoption of CT-based lung cancer screening protocols, it would be beneficial to reduce unnecessary thoracotomies, bronchoscopies, biopsies, and other invasive procedures. Similarly, breast cancer patients would benefit from an accurate, non-invasive predictor of pCR that facilitated more accurate and effective targeting of NAC.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
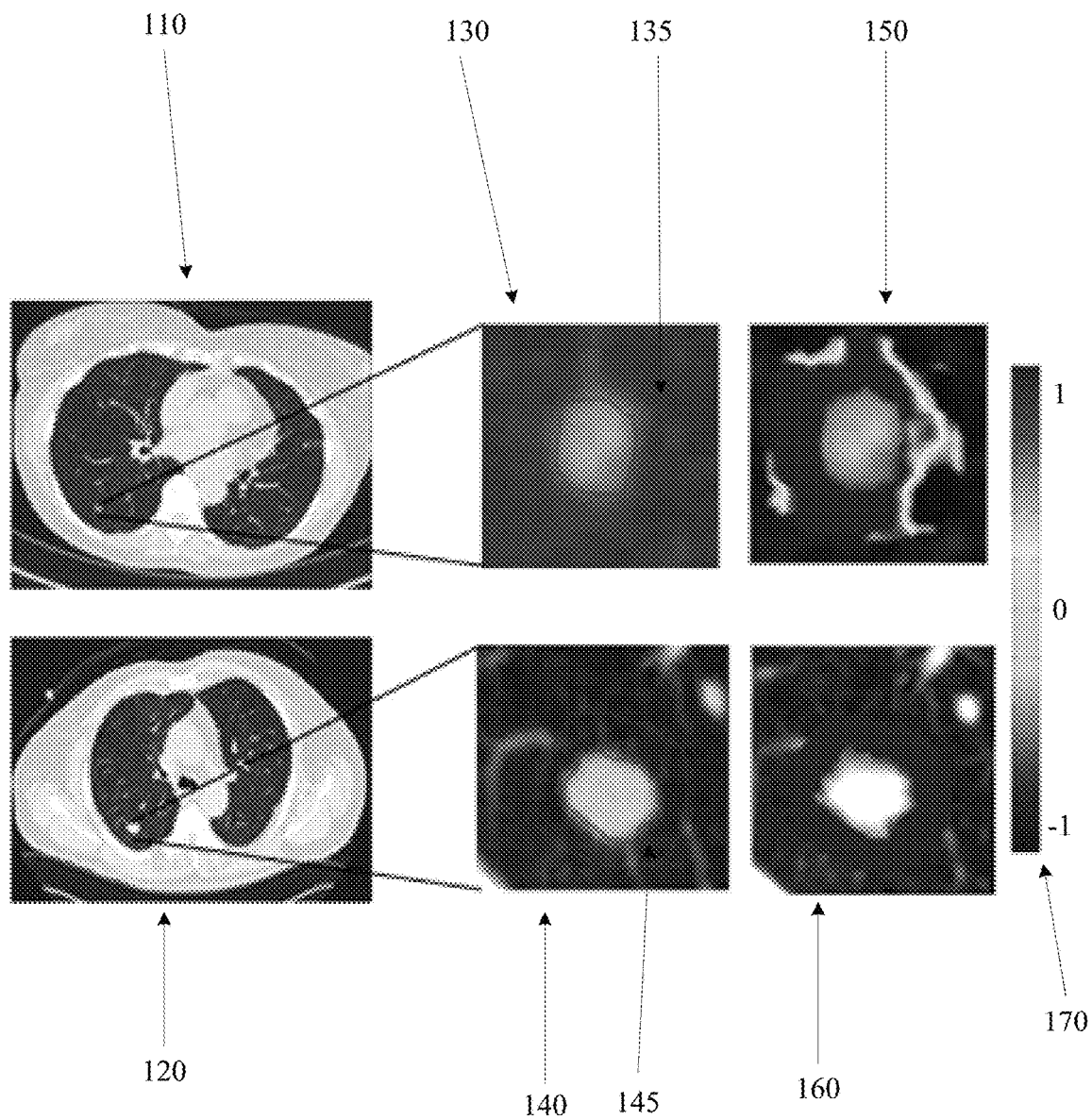
FIG. 1 illustrates textural features of a CT image of a granuloma and a carcinoma.

Variations in tumor invasiveness or morphology may be related to patient prognosis and outcome. Conventional methods of diagnosing cancer include visual histopathological examination of a biopsy to create a diagnostic profile based on variations in tumor morphology or invasiveness. However, invasive biopsies and surgical procedures may not always be a convenient or appropriate method for assessing nodules detected in a radiological image. Invasive biopsies and surgical resections cost money, take time, and put a patient at additional risk. A non-invasive approach that provided improved accuracy compared to conventional CT-based or MRI-based approaches would reduce the number of unnecessary interventions, reduce the dependency on repetitive or higher resolution radiological exams, offer a non-invasive means of assessing response to targeted therapies, and improve patient outcomes. Thus, a timely, non-invasive procedure that results in more accurate discrimination between benign tissue and malignant tissue, or that more accurately predicts a response to treatment, would offer reduced risk to patients while providing economic benefits to the health care system.

CT imagery is conventionally used to differentiate malignant nodules from other, non-cancerous nodules. A nodule may include a ground glass opacity (GGO) nodule or a solitary pulmonary nodule. However, it is difficult to distinguish lung AC nodules from benign Gr nodules, including nodules secondary to histoplasmosis infection, since both AC nodules and Gr nodules can have similar appearances and both can show increased activity on positron emission tomography (PET) or CT evaluation. For example, on chest a CT image, Gr nodules and AC nodules may both demonstrate a spiculated appearance. However, the vascular invasion and lymphangiogenesis in the perinodular habitat of AC is different from that of Gr. In particular, the perinodular zone or habitat of a malignant nodule may exhibit different molecular, radiological, or cellular alterations than the perinodular zone of a benign nodule. Additionally, neoplastic infiltration of malignant nodules may distort neighboring tissue in the perinodular zone. Malignant AC may also demonstrate different histologic patterns than benign Gr, including different lepidic, acinar, papillary, micropapillary, or solid histologic patterns.

Conventional methods of visually assessing nodule invasiveness based on CT imagery are subjective and yield intra and inter-reviewer variability. In one study, for example, more than 30% of suspicious nodules that underwent biopsy for histologic confirmation were determined to be benign Gr caused by prior histoplasmosis infection. Conventional CT approaches may focus exclusively on detection of lung nodules, or exclusively on diagnosing malignancy via CT scans. Example apparatus and methods discriminate benign Gr from malignant nodules by analyzing features extracted from a perinodular region associated with a nodule. The perinodular zone may be defined as the region surrounding the nodule extending a threshold distance from the nodule boundary. The perinodular zone may extend, in one embodiment, up to one centimeter from the nodule boundary. In other embodiments, the perinodular zone may extend a different distance from the nodule boundary. The perinodular zone may also be referred to as a peri-tumoral zone, or a peri-disease zone. For example, a region of tissue demonstrating a pathology may be bordered by a peri-disease zone extending a threshold distance from the region of tissue demonstrating the pathology. Example methods and apparatus distinguish benign granulomas secondary to histoplasmosis fungal infection from malignant carcinomas, and provide decision support in the diagnosis and treatment of patients exhibiting lung nodules in radiological imagery. Distinguishing benign fungal infection from malignant carcinoma facilitates reducing the number of surgical interventions performed that ultimately result in a diagnosis of histoplasmosis or other non-cancerous pathology.

MR imagery is conventionally used to image breast cancer tissue. NAC is often a first line of defense in the treatment of breast cancer. NAC is administered prior to surgery, and may reduce the extent of tumor burden and increase a patient's surgical options. The ideal outcome of NAC is pCR, which is strongly correlated with favorable prognosis and reduced recurrence of breast cancer compared to patients who exhibit partial or no pCR. However, fewer than 25% of breast cancer patients who undergo NAC will achieve pCR. Thus, more accurate, non-invasive prediction of pCR would offer reduced risk to patients while providing economic benefits to the health care system. Example methods and apparatus thus facilitate patients less likely to achieve pCR being spared costly, ineffective treatments, while patients more likely to achieve pCR may be more likely to receive appropriate treatments.

The occurrence of pCR in NAC recipients is dependent on tumor characteristics. Furthermore, the tissue surrounding a breast tumor or nodule (e.g. the perinodular zone) includes useful markers of NAC response. In particular, lymphocyte infiltration and immune response within the stroma are predictive of pCR in all breast cancer subtypes. Example methods and apparatus employ dynamic contrast-enhanced (DCE) MR imaging to image breast tissue demonstrating cancerous pathology. Example methods and apparatus detect pathologic markers of pCR in DCE-MR imagery and predict patient response to NAC treatment based, at least in part, on the detected pathologic markers. Example methods and apparatus detect pathological markers of pCR in DCE-MR imagery of a patient demonstrating breast cancer pathology by extracting and analyzing radiomic features from a perinodular zone associated with a tumor represented in the DCE MR imagery.

Example methods and apparatus more accurately distinguish malignant lung nodules from benign lung nodules by extracting and analyzing a set of features from a perinodular region associated with a lung nodule represented in a radiological image. Example methods and apparatus may also extract and analyze a set of features from the nodule to further distinguish benign lung nodules from malignant lung nodules. For example, example methods and apparatus may compute a probability that a nodule is a benign nodule based, at least in part, on the set of features extracted from the perinodular region, and the set of features extracted from the nodule. Since a more accurate distinction is made, example apparatus and methods thus predict patient outcomes in a more consistent and reproducible manner.

Example methods and apparatus predict patient outcomes more accurately than conventional methods by employing computerized textural and morphologic analysis of lung CT imagery to distinguish benign Gr from malignant tumors. Example methods and apparatus may segment a nodule from an image background. A spectral embedding gradient vector flow active contour (SEGvAC) model may be employed to segment the nodule from the image background. A perinodular region may be defined with respect to the nodule segmented from the image background. The perinodular region may extend a threshold distance from the nodule. Features may be extracted from the perinodular region. The features extracted from the perinodular region may include texture features. The texture features may include gradient-based texture features. Malignant lung tumors may induce irregular changes to vessel shapes within the perinodular region. Example methods and apparatus also detect and quantify differences in lymphatic vessel density within the perinodular region. Example methods and apparatus may also extract shape features or tortuosity features from the perinodular region, or from the nodule. Features extracted from the perinodular region or the nodule may facilitate improved detection and analysis of histologic patterns demonstrated by AC or other diseases, including lepidic patterns, acinar patterns, papillary patterns, micropapillary patterns, or solid patterns. Features extracted from the perinodular region or the nodule may facilitate capturing growth patterns of AC or other malignancies, including angiogenesis, tumor growth, invasion, or metastasis that constitute a neoplastic microenvironment around the nodule. A subset of extracted features may be selected using principal component analysis (PCA)-variable importance projection (VIP) analysis. The subset of extracted features may include features that are more discriminative than other, non-selected features. A classification of the nodule image may be generated using quadratic discriminant analysis (QDA) or linear discriminant analysis (LDA).

Carcinomas or other diseased tissue may have a more chaotic cellular architecture than Gr or other benign tissue. The chaotic cellular architecture may be correlated to an energy feature in an image. The energy feature may be represented as a texture feature. In some embodiments, the energy feature is more pronounced in a CT heatmap of a cancerous nodule than in a CT heatmap of a Gr because of the more chaotic cellular architecture of the cancerous nodule. FIG. 1 illustrates this property of cancerous nodules compared with Gr nodules that were caused by benign fungal infections. The chaotic cellular architecture may also be correlated to tortuosity features of vessels associated with a tumor or a nodule.

FIG. 1 illustrates example textural features that example methods and apparatus may use to distinguish benign nodules from malignant nodules. FIG. 1 illustrates a CT scan image 110 of a cancerous nodule identified as a carcinoma. FIG. 1 also illustrates a CT scan image 120 of a nodule identified as a Gr. FIG. 1 also illustrates a close-up view 130 of the cancerous nodule, along with a first perinodular zone 135. FIG. 1 also illustrates a close up view 140 of the granuloma, along with a second perinodular zone 145. FIG. 1 also illustrates a heatmap 150 of a Gabor feature of the cancerous nodule. The Gabor feature represents texture using a sinusoidal plane wave modulated Gaussian kernel function. FIG. 1 further illustrates a heatmap 160 of a Gabor texture feature of the benign granuloma. FIG. 1 also illustrates a scale 170 for reading the Gabor texture features.

Example methods and apparatus may train and test a classifier. For example, one embodiment may employ 3-fold cross validation for training a classifier and for testing the classifier. The classifier may be a support vector machine (SVM) classifier. For example, a human pathologist may manually delineate and classify one hundred nodules for a training set and thirty nodules for a testing set. Example methods and apparatus may classify the nodule image as a carcinoma, adenocarcinoma, or as a granuloma. Other classifications may be employed. Other sizes of training sets or sizes of testing sets may be employed. Example methods and apparatus may classify the nodule as having a threshold probability of achieving pCR after NAC treatment.

Example methods and apparatus may employ an SVM classifier in conjunction with PCA-VIP determined features to discriminate pathologies of interest (e.g. adenocarcinoma, granuloma, likely to achieve pCR). The classifier may be trained solely on the training set. A radial-based kernel function (RBF) may be applied to the training set. Members of the training set are defined in instance-label form $(x_i, y_i)$ where $x_i \in R^n$ and $y_i \in \{-1, 1\}$. The RBF function is formally defined as:

$$K(x_i, x_j) = \exp(\gamma \|x_i - x_j\|^2), \gamma > 0.$$

Example methods and apparatus thus improve on conventional methods by more accurately distinguishing between pathological and benign lung nodules. Example methods and apparatus distinguish granuloma from carcinoma with an accuracy of at least 0.77 area under the curve (AUC) when using texture features extracted from a smooth CT reconstruction kernel (rK) with a QDA SVM classifier. In contrast, conventional approaches using a sharp rK achieve only 0.72 AUC, conventional approaches using just Laws features achieve accuracies of approximately 0.61 AUC, while conventional approaches using just Gabor features achieve accuracies of approximately 0.68 AUC. Example methods and apparatus thus facilitate a significant, measurable increase in accuracy compared to conventional approaches. Example methods and apparatus may also predict response to NAC with an accuracy of at least 0.87 AUC.

By increasing the accuracy with which malignant nodules are distinguished from benign lung nodules, or by which response to treatment is predicted, example methods and apparatus produce the concrete, real-world technical effect of reducing the time required to evaluate medical imagery while increasing the accuracy of the evaluation. Additionally, example apparatus and methods increase the probability that at-risk patients receive timely treatment tailored to the particular pathology they exhibit. Example methods and apparatus may also reduce the number of invasive procedures needed to accurately characterize nodules. The additional technical effect of reducing the expenditure of resources and time on patients who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
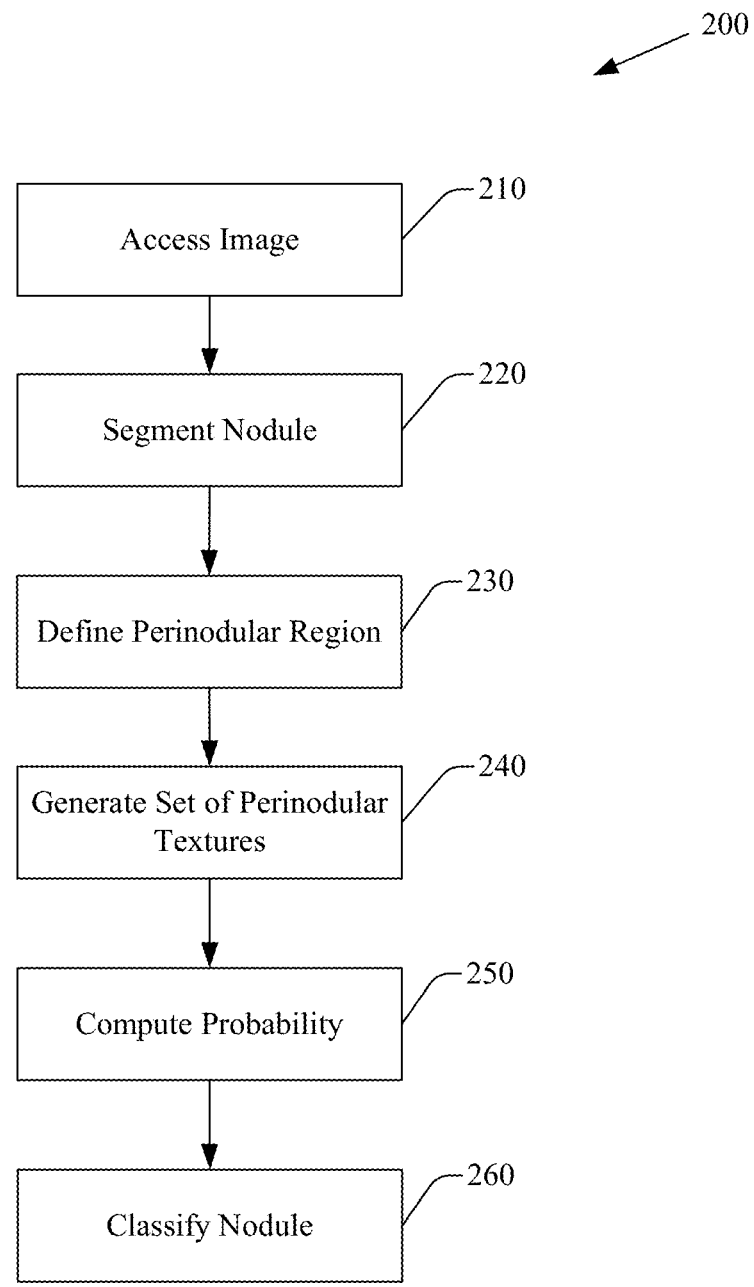
FIG. 2 illustrates an example method of characterizing a nodule in a region of tissue.

FIG. 2 illustrates an example computerized method 200 for characterizing a nodule in a region of tissue. Method 200 includes, at 210, accessing an image of a region of tissue. Accessing the image may include accessing a no-contrast CT image of a region of lung tissue demonstrating cancerous pathology. Accessing the image may also include accessing another type of medical image of a region of tissue demonstrating a different, non-cancerous pathology. Accessing the image may include retrieving electronic data from a computer memory, receiving a computer file over a computer network, or other computer or electronic based action. In one embodiment, the image is a 1 mm to 5 mm thick, no-contrast chest CT image. In one embodiment, the number of slices per scan may range from 126 to 385, and a slice may have an XY planar resolution of 512 pixels by 512 pixels, with a 16 bit gray scale resolution indicated in Hounsfield Units (HU). In another embodiment, other image types, resolutions, scales, slices per scan, or image dimensions may be used.

Method 200 also includes, at 220, segmenting a nodule in the image. Segmenting the nodule includes defining a nodule boundary. The nodule boundary may be extracted from the image. The nodule may be automatically segmented by distinguishing nodule tissue within the image from the background of the image. In one embodiment, the nodule tissue may be automatically distinguished using SEGvAC segmentation. In another embodiment, other segmentation approaches may be employed, including threshold based segmentation, deformable boundary models, active-appearance models, active shape models, graph based models including Markov random fields (MRF), min-max cut approaches, or other image segmentation approaches. In another embodiment, the nodule may be manually segmented.

SEGvAC segmentation includes separating the lung region from the surrounding anatomy in the image. A non-linear embedding representation of the lung may be employed to separate the image of the lung from the surrounding thoracic anatomy. The SEGvAC approach also includes removing non-nodule structures from the image using a rule-based classifier. The SEGvAC approach further includes extracting the nodule surface from the image using active contour based segmentation. Example methods and apparatus employing a SEGvAC approach improve on conventional approaches by eliminating segmentation errors caused by both pleura and vessel attached nodules by separating lung tissues and removing non-nodule structures.

SEGvAC segmentation employs a spectral embedding based active contour. Spectral embedding (SE) is a non-linear dimensional reduction method that forms an affinity matrix via a pre-specified kernel function. The kernel function facilitates a mapping of an original set of image features or intensities to a new kernel space where spectral decomposition may be applied to the corresponding graph Laplacian. An individual pixel from the original lung CT image is then represented by the corresponding value of the eigenvectors obtained by spectral decomposition. SE representation of the lung provides strong gradients at the margin of the nodules which facilitate an active contour model to stop evolving at the nodule boundary. The SEGvAC approach employed by example methods and apparatus further includes a gradient vector flow field (GVF) active contour. The GVF forces are calculated for the image domain. The GVF forces drive the active contour.

In one embodiment, the SEGvAC segmentation approach includes isolating lung regions from surrounding anatomy illustrated in the CT image to generate an initial lung mask. Example methods and apparatus identify an optimal threshold to separate body voxels from non-body voxels. A non-body voxel is a low density voxel representing lung and surrounding air. The initial lung mask is further refined by applying morphological hole filling to the logical complement of the initial lung mask.

Upon extraction of the initial region of interest (e.g. lung region) from the CT image, example methods and apparatus may perform an automatic segmentation of the nodule. Example methods and apparatus employ an active contour scheme to segment the nodule. In one embodiment, the image plane $\Omega = R^2$ is partitioned into two regions by a curve $Y$. The foreground region of the image plane is defined as $\Omega_1$ and the background region of the image plane is defined as $\Omega_2$. Thus, the image plane is comprised of the union of regions of interest, background, and evolving contour ($\Omega = \Omega_1 \cup \Omega_2 \cup Y$).

In simplified form, the energy functional of an edge-based active contour is defined as $$E = \alpha E_1 + \beta E_2 \quad \text{(eq. 1)}$$

where $E_2$ refers to internal forces used to keep the integrity and elasticity of the contour and where $E_1$ is the image force.

The image force $E_1$ is defined as $$E_1 = \int_Y g(v(c)) dc \quad \text{(eq. 2)}$$

where $c=(x,y)$ corresponds to a voxel in the two dimensional (2D) image plane, $v(c)$ is the intensity value of the voxel c, and $g(v(c))$ is defined as $$g(v(c)) = \frac{1}{1 + \psi(v(c))}. \quad \text{(eq. 3)}$$

The gradient function $\psi(v(c))$ is conventionally calculated by a gray level gradient. Example methods and apparatus employ a tensor gradient function derived from the spectral embedding representation. By using the tensor gradient function, example methods and apparatus facilitate the generation of improved region and boundary-based statistics, and stronger gradients, compared to conventional approaches.

Example methods and apparatus employ a GVF active contour. The GVF forces calculated for the image domain are used to drive the active contour. Active contours driven by GVF forces do not need to be initialized very closely to the boundary. The GVF forces are calculated by applying generalized diffusion equations to both components of the gradient of an image edge map, where the image edge map is of the original CT image. In one embodiment, the SEGvAC approach is initialized using a single point and click on a region of interest (e.g. nodule). In another embodiment, the SEGvAC approach may be initialized automatically.

In one embodiment, before employing the SEGvAC approach, example methods and apparatus may employ a rule-based classifier to remove unwanted structures from the image based on geometric properties of the unwanted structures. The geometric properties of the unwanted structures may be 3D geometric properties. The 3D geometric properties may include bounding box measures and elongation of 3D structures defined as the length of the major axis of the nodule divided by the length of the minor axis of the nodule. Lung nodules are frequently 5 mm to 30 mm long. Thus, 3D structures that do not fit this size may be eliminated using the rule-based classifier. Candidate objects for inclusion or exclusion may be examined in terms of convexity or elongation measures for distinguishing vessel-like structures from more convex or sphere-like objects. In one embodiment, a set of morphological operations, including erosion and closing operations, may be employed to filter objects associated with vessel-connected nodules. By removing unwanted structures, example methods and apparatus facilitate improving the performance of a computer aided diagnosis (CADx) system by reducing the computational resources required to analyze the perinodular zone.

Method 200 also includes, at 230, defining a perinodular region associated with the nodule. In one embodiment, defining the perinodular region includes generating an outer perinodular boundary by dilating the nodule boundary a threshold amount. In one embodiment, the threshold amount is from 5 mm to 7 mm. In another embodiment, another, different threshold amount may be used. For example, the threshold amount may be from 3.5 mm to 5 mm. In one embodiment, the threshold amount is user adjustable. The threshold amount may be based on a unit of distance (e.g. mm) or may be based on a pixel size, an image resolution, a number of pixels, or other unit of measurement. For example, in one embodiment in which the CT image has a pixel size of 0.7 mm center to center, the threshold amount may be defined as 7 pixels. Thus, in this example, a mask of the nodule defined by the nodule boundary may be dilated by seven pixels. Defining the perinodular region further includes subtracting the nodule from the region defined by the outer perinodular boundary. Thus, for example, in one embodiment, the perinodular region may be bounded by the outer perinodular boundary and the nodule boundary.

Figure 3:
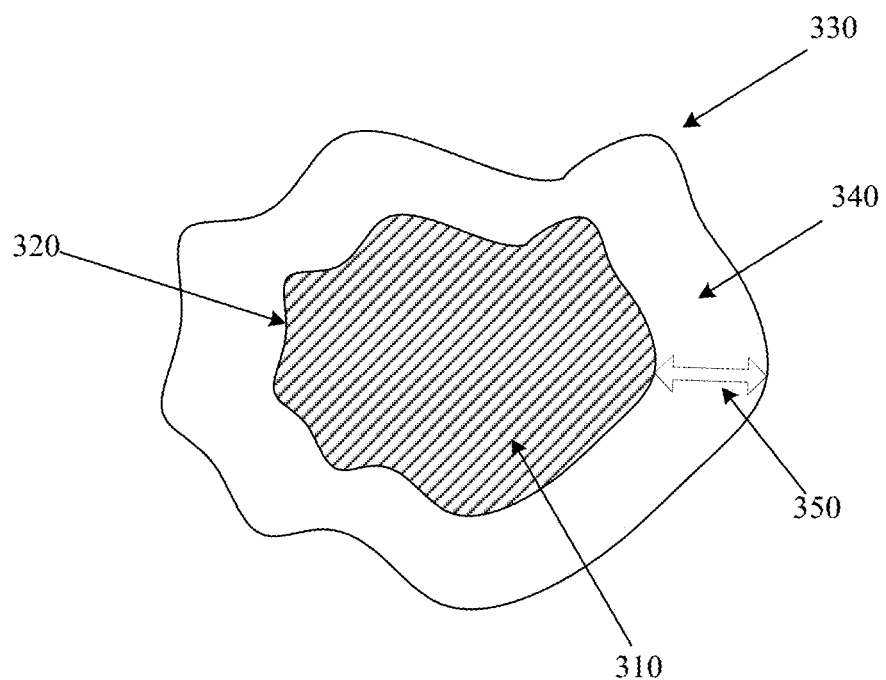
FIG. 3 illustrates a perinodular zone associated with a nodule.

FIG. 3 illustrates an example perinodular region 340 associated with a nodule 310. Perinodular region 340 is bounded by outer perinodular boundary 330 and nodular boundary 320. In one embodiment, example methods and apparatus dilate nodule boundary 310 by an amount 350, resulting in the outer perinodular boundary 330.

In another embodiment, the perinodular boundary may be generating using other techniques. For example, the perinodular boundary may be defined as a function of a property of the nodule. The property of the nodule may include, for example, a diameter, a radius, a perimeter, an area, a volume, or other property of the nodule. The function may define the perinodular region as, for example, a dilation of the nodule boundary, where the dilation ratio is defined by a magnitude of an axis of the nodule. In another embodiment, the perinodular boundary may be defined as a disc of a threshold radius defined about the centroid of the nodule, or defined on the focal points of an elliptical representation of the nodule. In one embodiment, the perinodular boundary may be manually defined. Other approaches or combinations of approaches may be used to define the perinodular boundary.

In one embodiment, method 200, at 230, includes removing pixels having less than a threshold level of HU from the perinodular zone. Lung parenchyma have HU values of approximately −500. In one embodiment, the threshold level is −900 HU. Removing pixels having less than a threshold level of HU from the perinodular zone facilitates radiomic analysis of the perinodular zone by removing confounding information from the image being analyzed, or by reducing the amount of computational resources required to extract features from the perinodular zone compared to conventional approaches. For example, pixels representing air, which has an HU value of approximately −1000, may be removed from the image. Other tissue, including bone, may also be removed. For example, pixels representing cancellous bone (+700 HU) or cortical bone (+3000 HU) may be removed.

Method 200 also includes, at 240, generating a set of perinodular texture features from the perinodular region associated with the nodule. Generating the set of perinodular texture features includes extracting a set of texture features from the perinodular region. The set of texture features includes a gray-level statistical feature, a steerable Gabor feature, a histogram of oriented gradient (HoG) feature, a Haralick feature, a Law feature, a Law-Laplacian feature, a local binary pattern (LBP) feature, an inertia feature, a correlation feature, a difference entropy feature, a contrast inverse moment feature, or a contrast variance feature. In one embodiment, the set of texture features includes at least twenty four texture features. In other embodiments, other numbers or types of texture features may be extracted. The set of texture features may also include a co-occurrence of local anisotropic gradient orientations (CoLIAGe) features.

In one embodiment, generating the set of perinodular texture features includes selecting a subset of texture features from the set of texture features. In one embodiment, the subset of texture features is selected by reducing the set of texture features using a PCA-VIP approach. In another embodiment, first order statistics may be derived from different radiomic descriptor families (e.g. Haralick, Laws Energy, HoG, or Gabor). The subset of texture features may be selected after running one-hundred iterations of three-fold cross validation using an Area Under the receiver-operating characteristic Curve (AUC) using a QDA classifier. The most discriminative features may then be identified using a Feed Forward Feature Selection (FFFS) approach. In one embodiment, the subset of texture features includes a kurtosis of a Haralick feature, a mean of the Haralick feature, a kurtosis of a Laplacian, and a mean of a Law feature. In another embodiment, the subset of texture features includes a mean of a Gabor feature, a standard deviation of the Gabor feature, a mean of the Gabor feature, and a median of an HoG.

In another embodiment, example methods and apparatus employ a PCA of the set of texture features to select the subset of texture features from the set of texture features. The subset of texture features may achieve a threshold level of discriminability. For example, the PCA may select one energy feature and one Gabor feature that are the most discriminative, based on a particular set of CT images, for distinguishing Gr from AC. The subset of texture features may include as few as two texture features. The level of discriminability may be user adjustable. For example, in a first clinical situation, a subset of texture features that achieves 0.84 AUC accuracy in distinguishing benign Gr from AC may be acceptable. In another embodiment, a 0.77 AUC may be acceptable. A feature may be considered to have a desirable level of discriminability when the means of two separate classes are more than a threshold distance from each other, and where the variance of a class is less than a threshold distance, in comparison to the distance between the means. In one embodiment, the Fisher criterion, which is the squared difference of the means divided by the sum of the variances, may be used to quantitatively establish a desirable level of discriminability.

Method 200 also includes, at 250, computing a probability that the nodule is benign. Method 200 computes the probability based, at least in part, on the set of perinodular texture features. In one embodiment, computing the probability that the nodule is benign includes computing the probability that the nodule is a benign Gr secondary to histoplasmosis infection. In another embodiment, computing the probability that the nodule is benign includes computing the probability that the nodule is another type of benign nodule. Example methods and apparatus may also compute a probability that the nodule is malignant. Example methods and apparatus may also compute a probability that the nodule will achieve pCR in response to NAC. Example methods and apparatus may also compute a probability that a different type of cancerous pathology identified in the image will respond to a different treatment.

Method 200 also includes, at 260, classifying the nodule. Classifying the nodule may include controlling a CADx system to generate a classification of the nodule represented in the image. The classification may be based, at least in part, on the set of perinodular texture features or the probability. In one embodiment, the CADx system generates the classification of the image of the nodule using a QDA classifier. In another embodiment, the CADx system may generate the classification using other, different types of classifier. The classifier may be an SVM classifier trained and tested on a set of images of pre-classified nodules. The set of images of pre-classified nodules may include an image of a region of tissue demonstrating adenocarcinoma pathology annotated by an expert pathologist. In one embodiment, controlling the CADx system to generate the classification of the nodule based, at least in part, on the set or perinodular texture features or the probability, includes classifying the image of the nodule as malignant adenocarcinoma or benign Gr secondary to histoplasmosis infection. In another embodiment, example methods and apparatus control the CADx system to generate a classification of the nodule based, at least in part, on the set of perinodular texture features, or on the probability that the nodule will achieve pCR.

Example methods and apparatus facilitate more accurate characterization of nodules found in CT images than conventional approaches. Example methods and apparatus thus improve on conventional methods by characterizing nodules as benign Gr secondary to histoplasmosis infection, carcinomas, or adenocarcinomas, with greater accuracy and with less subjective variability than conventional methods. Example methods and apparatus therefore facilitate more judicious application of biopsies and surgical resection in a population undergoing CT screening for lung cancer. Example methods and apparatus also facilitate more accurate prediction of achieving pCR from DCE-MR imagery of tissue demonstrating breast cancer pathology. Example methods and apparatus therefore facilitate more efficient and accurate targeting and application of NAC treatment.

Using a more appropriately determined and applied treatment may lead to less therapeutics being required for a patient or may lead to avoiding or delaying a biopsy, a resection, or other invasive procedure. When regions of cancerous tissue, including nodules detected in CT scans, or nodules detected in DCE-MRI are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effect of improving patient outcomes.

While FIG. 2 illustrates various actions occurring in serial, it is to be appreciated that various actions illustrated in FIG. 2 could occur substantially in parallel. By way of illustration, a first process could delineate a nodule in a CT image, a second process could define a perinodular zone in the CT image, and a third process could extract perinodular texture features from the CT image. While three processes are described, it is to be appreciated that a greater or lesser number of processes could be employed and that lightweight processes, regular processes, threads, and other approaches could be employed.

In one embodiment, method 200 may also include other steps. Method 200 may include accessing a DCE-MR image of a region of breast tissue. Method 200 may also include other steps when defining the perinodular region. In one embodiment, defining the perinodular region includes segmenting a breast wall from the image, and removing or subtracting the segmented breast wall from the image. Segmenting the breast wall may be performed manually, or may be performed automatically. Breast cancer nodules may occur within a threshold distance to the breast wall. Generating the perinodular zone may thus include surrounding empty space or the hyper intense interface between breast and air. Example methods and apparatus segment the breast wall to exclude areas outside the breast from the perinodular zone, thus increasing the accuracy with which nodules may be characterized, and reducing the computational resources required to extract and analyze features from the perinodular zone.

In one embodiment, method 200 generates the outer perinodular boundary by dilating the nodule boundary a threshold amount. For example, when analyzing breast cancer tissue, the perinodular boundary may be dilated a threshold amount of 3.5 mm to 5 mm, or may be dilated from 7 mm to 10 mm. The threshold amount may be determined as a function of tumor size, invasiveness, or other factors. Method 200 may also generate a perinodular region by subtracting the nodule from the region defined by the outer perinodular boundary.

In one embodiment, method 200 computes a probability that the nodule will achieve pCR based, at least in part, on the set of perinodular texture features. In one embodiment the set of perinodular texture features may be extracted from the DCE-MR image at two post-contrast phases. The set of perinodular texture features may be extracted at a first, initial post-contrast phase, including a first scan collected following intravenous contrast agent injection. The set of perinodular texture features may also be extracted during a second, later phase in which the contrast enhancement intensity is at a threshold peak contrast level. In one embodiment, the set of perinodular texture features extracted during the initial post-contrast phase includes a Laws spot-wave standard deviation feature, a CoLIAGe sum entropy-kurtosis feature, a Laws wave-wave skewness feature, a Laws wave-wave standard deviation feature, and a Gabor standard deviation feature. In one embodiment, the set of perinodular features extracted during the peak contrast phase includes, a CoLIAGe difference-variance skewness feature, a Laws edge-ripple standard deviation feature, a Haralick inverse difference moment skewness feature, a Laws level-ripple mean feature, and a CoLIAGe difference entropy kurtosis feature. CoLIAGe features include statistics of dominant gradient orientation co-occurrence matrices. Haralick calculations computed on first derivative gradient orientations may be extracted from the CoLIAGe features. Other features may also be extracted, and other statistics may be calculated.

In one embodiment, method 200 also controls the CADx system to generate a classification of the nodule. The classification of the nodule may be based, at least in part, on the set of perinodular texture features, or the probability that the nodule will achieve pCR. The classification of the nodule facilitates the timely, efficient, and accurate application of NAC.

Figure 4:
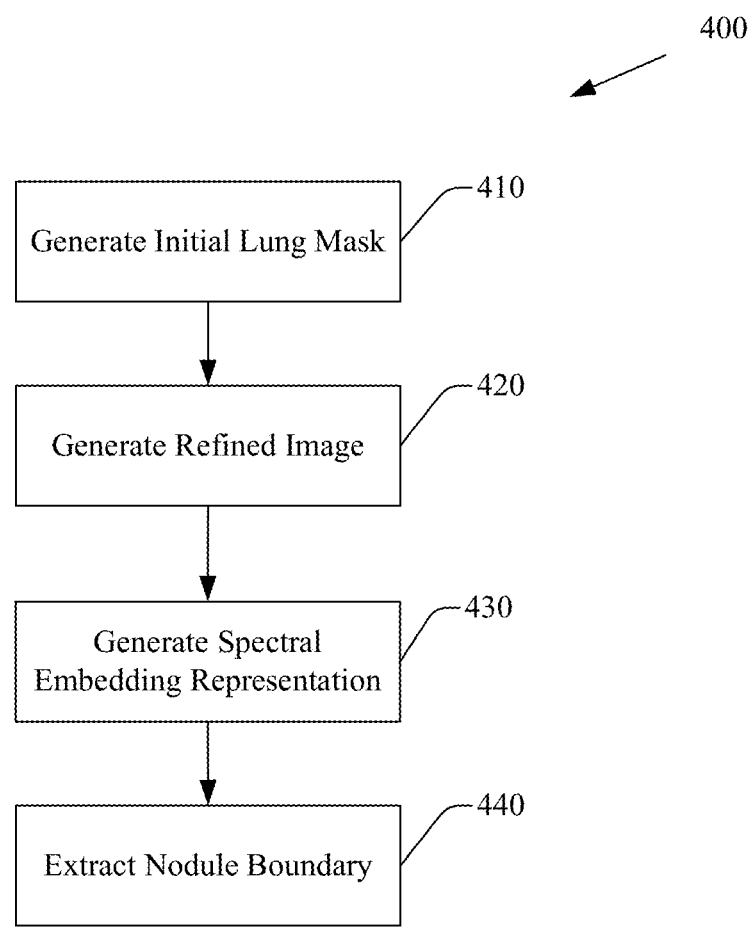
FIG. 4 illustrates an example method for segmenting a nodule.

FIG. 4 illustrates an example method 400 for distinguishing nodule tissue in a CT image from a background of the image using a SEGvAC approach. Method 400 is suitable for use by example methods and apparatus described herein, including method 200, method 500, method 600, or apparatus 700. Method 400 includes, at 410 generating an initial lung mask. In one embodiment, generating the initial lung mask includes separating a lung region represented in the image from surrounding lung anatomy. In one embodiment, generating the initial lung mask includes refining the initial lung mask by applying morphological hole-filling to a logical complement of the initial lung mask.

Method 400 also includes, at 420, generating a refined image. Generating the refined image includes removing a non-granuloma structure from the initial lung mask using a rule-based classifier. In one embodiment, the rule-based classifier selects a non-granuloma structure to remove from the initial lung mask based on a convexity measure of the non-granuloma structure, or on an elongation measure of the non-granuloma structure. The rule-based classifier may select a non-granuloma structure to remove based on 3D geometric properties of structures in the perinodular zone. The 3D properties may include bounding box measures and elongation of the 3D structure defined as the length of the major axis divided by the length of the minor axis. In one embodiment, 3D structures that do not fit within a size criteria range of 5 mm to 30 mm are removed by the rule-based classifier. In another embodiment, morphological operations, including erosion operations or closing operations, are used to isolate vessel-connected nodules.

Method 400 also includes, at 430, generating a spectral embedding (SE) representation by projecting at least one refined image into a 3D SE space. In one embodiment, generating an SE representation includes forming an affinity matrix via a pre-specified kernel function. The kernel function facilitates mapping a set of image features to a new kernel space, where spectral decomposition is applied to a corresponding graph Laplacian. A pixel in the CT image is then represented by a corresponding value of an eigenvector obtained via the spectral decomposition step.

Method 400 also includes, at 440, extracting a nodule boundary from the SE representation. Extracting the nodule boundary may include calculating a tensor gradient function derived from the SE representation. In one embodiment, extracting the nodule boundary from the SE representation includes extracting the nodule boundary using a gradient vector flow field (GVF) active contour model. A GVF force drives the active contour. In one embodiment, the GVF force is calculated based on a generalized diffusion equation applied to a component of an image edge map of the CT image of the region of lung tissue.

Figure 5:
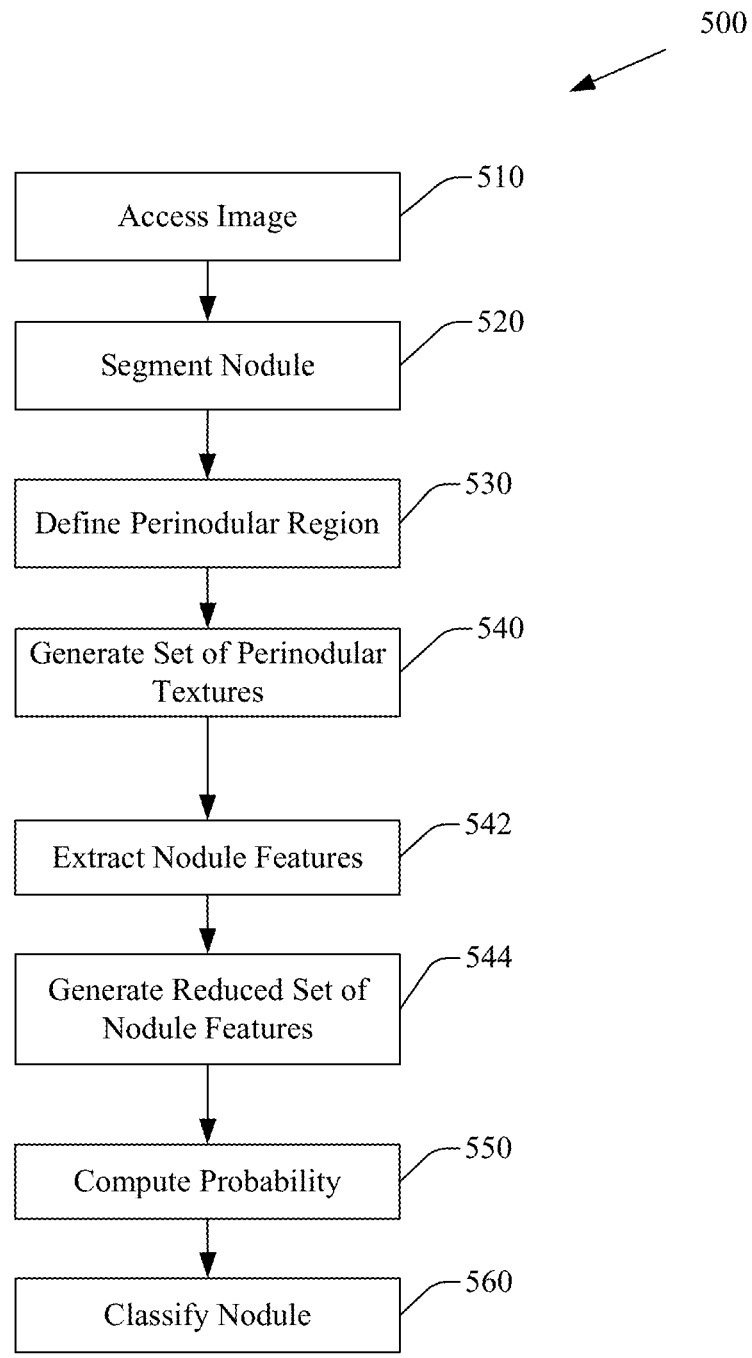
FIG. 5 illustrates an example method of characterizing a nodule in a region of lung tissue.

FIG. 5 illustrates an example method 500 for characterizing a nodule in a region of lung tissue. Method 500 is similar to method 200 but includes additional actions. Method 500 includes actions 510, 520, 530, and 540 which are similar to actions 210, 220, 230, and 240 described above with respect to method 200.

Method 500 also includes, at 542, extracting a set of nodule features from the nodule. In one embodiment, extracting the set of nodule features includes extracting a set of shape features from the image of the nodule. The set of shape features includes a location feature, a size feature, a width feature, a height feature, a depth feature, a perimeter feature, an eccentricity feature, an eccentricity standard deviation, a compactness feature, a roughness feature, an elongation feature, a convexity feature, an extend feature, an equivalent diameter feature, or a sphericity feature. The location feature describes the spatial information of a pixel in the image of the nodule, the size feature describes the number of pixels within the segmented image of the nodule, and the perimeter feature describes the distance around the boundary of the segmented nodule. The eccentricity feature describes the eccentricity of an ellipse that has the same second moments as the nodule. The compactness feature describes the isoperimetric quotient of the nodule. The roughness feature describes the perimeter of a lesion in a slice of the image of the nodule divided by the convex perimeter of the lesion. The elongation feature describes the ratio of minor axis to the major axis of the image of the nodule, and the convexity feature describes the ratio of a tumor image slice to the convex hull of the tumor. The extend feature describes the ratio of pixels in the tumor region to pixels in the total bounding box. The equivalent diameter feature describes the diameter of a circle having the same area as a tumor image slice, and the sphericity feature describes the three-dimensional compactness of the nodule. In one embodiment the set of shape features includes at least twenty-four shape features. In another embodiment, the set of shape features may include other numbers of shape features, or other, different shape features. A feature may be calculated in 3D space, or in two dimensional (2D) space. For example, width, height, depth, or sphericity features may be calculated in 3D space.

In one embodiment, extracting the set of nodule features from the nodule includes extracting a second set of texture features. The second set of texture features includes a gray-level statistical feature, a steerable Gabor feature, a Haralick feature, a Law feature, a Law-Laplacian feature, a local binary pattern (LBP) feature, inertia, a correlation feature, a difference entropy feature, a contrast inverse moment feature, or a contrast variance feature. In one embodiment, the second set of texture features includes at least twenty four texture features. In other embodiments, other numbers or types of texture features may be extracted.

Method 500 also includes, at 544, generating a reduced set of nodule features. In one embodiment, generating a reduced set of nodule features includes selecting a subset of shape features from the set of shape features. In one embodiment, the subset of shape features includes eccentricity, eccentricity standard deviation, or elongation features. In another embodiment, the subset of shape features may include other, different shape features. The subset of shape features may be selected from the set of shape features using PCA feature ranking or PCA-VIP feature ranking.

Method 500 also includes, at 550, computing a probability that the nodule is benign. In one embodiment, computing the probability that the nodule is benign includes computing the probability that the nodule is a benign Gr secondary to histoplasmosis infection. In another embodiment, computing the probability that the nodule is benign includes computing the probability that the nodule is another type of benign nodule. Example methods and apparatus may also compute a probability that the nodule is malignant. Example methods and apparatus may also compute a probability that the nodule will achieve pCR in response to NAC. Example methods and apparatus may also compute a probability that a different type of cancerous pathology identified in the image will respond to a different treatment. Method 500 computes the probability based, at least in part, on the reduced set of nodule features and the set of perinodular texture features.

Method 500 also includes, at 560, controlling the CADx system to generate a classification of the image of the nodule. In one embodiment, the CADx system classifies the nodule as a benign Gr secondary to histoplasmosis infection, or as a malignant adenocarcinoma. The CADx system may employ an SVM to generate the classification. The classification may be based, at least in part, on the subset of texture features and the subset of shape features. Basing the classification on both the subset of texture features and the subset of shape features improves on conventional approaches by increasing the accuracy with which the image of the may be classified. In one embodiment, the CADx system generates the classification of the image of the nodule using an LDA classifier or a QDA classifier. The LDA classifier or the QDA classifier may be trained or tested on a set of images pre-classified as Gr or adenocarcinoma.

In one embodiment, example methods and apparatus may also automatically segment vessels associated with the nodule. For example, method 500 may identify a centerline of a vessel and branching points associated with the vessel. Method 500 may identify the centerline or branching points using a fast marching approach. Method 500 calculates the torsion for a vessel segment using a distance metric. The torsion of a vessel segment is defined as 1–(Distance/Length) where distance is the Euclidean distance of the start and end point of the segment, and where length is the number of voxels along the vessel segment. Method 500 also extracts the curvature of a vessel segment. Curvature at a voxel of a vessel segment is proportional to the inverse of an osculating circle's radius. The osculating circle is fitted to a collection of three neighboring points along the centerline of a vessel. For a plurality of points along the center line of a vessel, method 500 fits a circle to compute the curvature of a specific point. Method 500 then computes mean and standard deviation of the curvature for points along the vessel. Method 500 may also capture branching statistics associated with the vessel.

Method 500 may then extract a set of tortuosity features from the image of the nodule. The tortuosity features describe vessels associated with the nodule. The set of tortuosity features includes the mean of torsion of a vessel segment, or the standard deviation of torsion of a vessel segment. The set of tortuosity features also includes the mean and standard deviation of the mean curvature of a group of vessel segments. The set of tortuosity features also includes the mean and standard deviation of the standard deviation of a vessel segment curvature and a total vessel segment length. The set of tortuosity features may also include branching statistics associated with the vessel. In one embodiment, the set of tortuosity features includes at least seven tortuosity features. In another embodiment, the set of tortuosity features may include other numbers of tortuosity features, or other, different tortuosity features. Method 500 may also select of subset of tortuosity features from the set of tortuosity features. Method 500 may also include controlling the CADx system to generate the classification of the image of the nodule based, at least in part, on the subset of tortuosity features, the subset of texture features and the subset of shape features.

Figure 6:
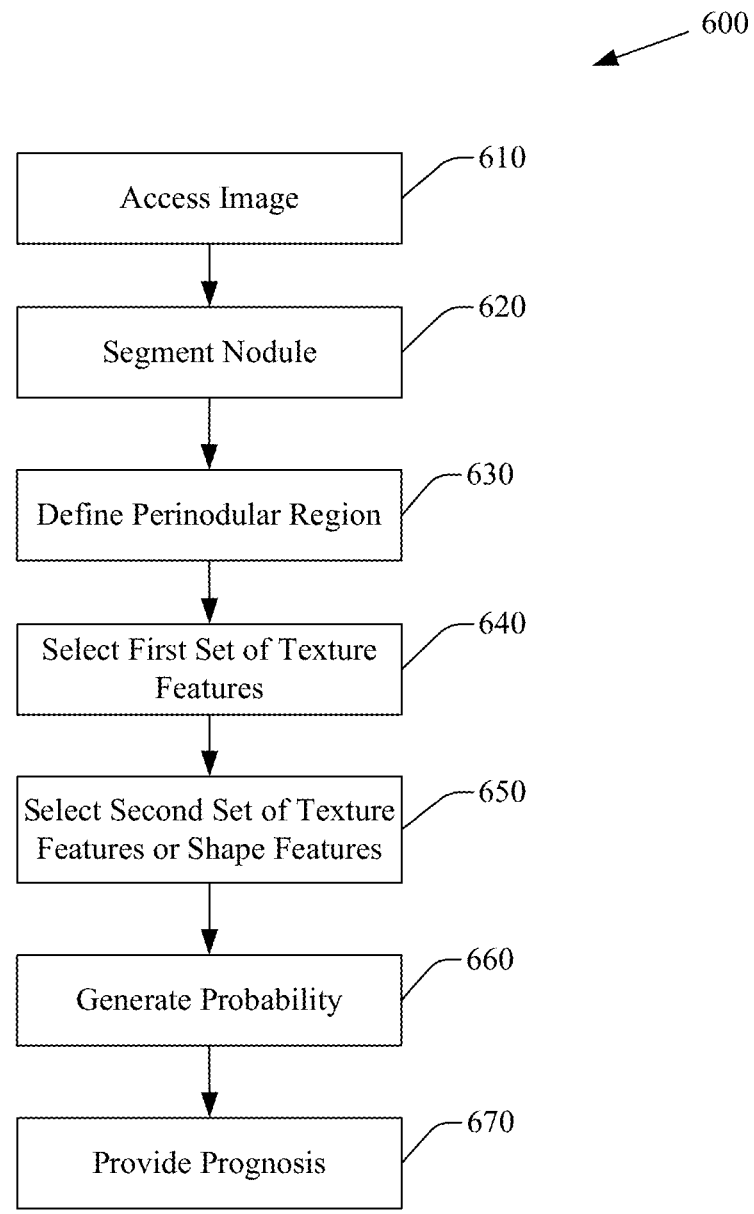
FIG. 6 illustrates an example method of characterizing a nodule in a region of lung tissue.

FIG. 6 illustrates an example method 600 for distinguishing benign tumors from malignant tumors in chest CT images. Method 600 includes, at 610 accessing an image of a region of tissue demonstrating cancerous pathology. In one embodiment, the image is a 1 mm to 5 mm thick, no-contrast chest CT image. In another embodiment, other image types or image dimensions may be used. Accessing the image may include retrieving electronic data from a computer memory, receiving a computer file over a computer network, or other computer or electronic based action.

Method 600 also includes, at 620, segmenting a nodule in the image from the background of the image. Segmenting the nodule in the image from the background of the image involves identifying the portion of the image that represents the nodule to distinguish that portion from the background. In one embodiment, the nodule is automatically segmented from the background of the image. In another embodiment, a human pathologist manually delineates the nodule from the background of the image. In another embodiment, vessels associated with the nodule are also segmented. The nodule may be segmented using SEGvAC segmentation.

Method 600 also includes, at 630, defining a perinodular region. The perinodular region may be based, at least in part, on the nodule. The perinodular region may be defined by dilating a boundary of the nodule, and subtracting the nodule from the region defined by the dilated boundary of the nodule.

Method 600 also includes, at 640, selecting a first set of texture features from the perinodular region. In one embodiment, the first set of texture features may include a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, or a contrast variance feature. In another embodiment, other, different texture features may be selected.

Method 600 also includes, at 650, selecting a second set of texture features or a set of shape features from the nodule. The set of shape features may include a location feature, a size feature, a perimeter feature, an eccentricity feature, an eccentricity standard deviation, a compactness feature, a roughness feature, an elongation feature, a convexity feature, an equivalent diameter feature, a radial distance feature, an area feature, or a sphericity feature. The second set of texture features may include a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, or a contrast variance feature. In another embodiment, other, different texture features may be selected.

In one embodiment, method 600 may also include selecting a set of tortuosity features from the perinodular region. The set of tortuosity features may include the mean of torsion of a vessel segment, or the standard deviation of torsion of a vessel segment. The set of tortuosity features may also include the mean and standard deviation of the mean curvature of a group of vessel segments. The set of tortuosity features may also include the mean and standard deviation of the standard deviation of a vessel segment curvature and a total vessel segment length. In one embodiment, the set of tortuosity features includes at least seven tortuosity features. In another embodiment, the set of tortuosity features may include other numbers of tortuosity features, or other, different tortuosity features.

Method 600 also includes, at 660, generating a probability that the nodule is a benign Gr. Generating the probability may include generating a classification for the nodule based, at least in part, on the first set of texture features and the second set of texture features, the set of shape features, or the set of tortuosity features. In one embodiment, the classification is made based on the first set of texture features. In another embodiment, the classification is based on the set of shape features. In still another embodiment, the classification is based on a subset of the first set of texture features, a subset of the set of shape features, a subset of the second set of texture features, and a subset of the set of tortuosity features. The subset of the first set of texture features may be selected from the first set of texture features using PCA-VIP or PCA. The subset of the second set of texture features may be selected from the second set of texture features using PCA-VIP or PCA. The subset of the set of shape features may be selected from the set of shape features using PCA-VIP or PCA. The subset of the set of tortuosity features may be selected from the set of tortuosity features using PCA or PCA-VIP. The subset of shape features, the subset of the first set texture features, the subset of the second set of texture features, or the subset of tortuosity features may be selected to achieve a threshold level of accuracy when classifying tumors. In one embodiment, method 600 classifies the tumor as a carcinoma or a Gr. In another embodiment, the tumor is classified as frank invasive, minimally invasive, or non-invasive. The classification may be made by a CADx system using an SVM, a QDA classifier, or an LDA classifier.

Method 600 also includes, at 670, providing a prognosis prediction based on the probability. For example, method 600, at 660, may provide a probability that the nodule is benign, and method 600 at 670, may provide a prognosis prediction based on the probability. Method 600 may, alternately, provide a probability that the nodule is malignant.

In one example, a method may be implemented as computer executable instructions. Thus, in one example, a computer-readable storage medium may store computer executable instructions that if executed by a machine (e.g., computer) cause the machine to perform methods described or claimed herein including method 200, method 400, method 500, and method 600. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 7:
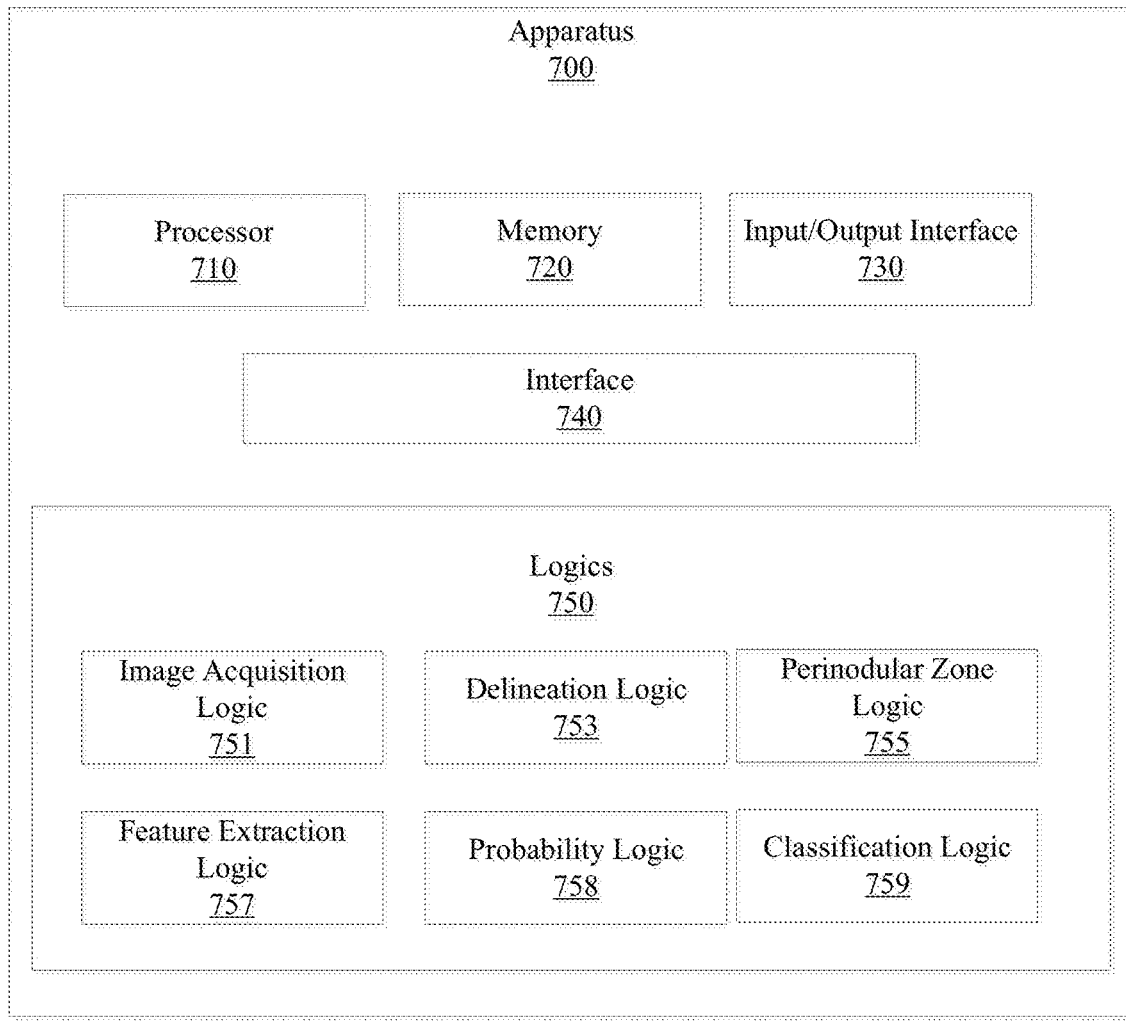
FIG. 7 illustrates an example apparatus that classifies a region of tissue in an image.

FIG. 7 illustrates an example apparatus 700 for classifying a region of tissue in an image. Apparatus 700 includes a processor 710, a memory 720, an input/output (I/O) interface 730, a set of logics 750, and an interface 740 that connects the processor 710, the memory 720, the I/O interface 730, and the set of logics 750. The set of logics 750 includes an image acquisition logic 751, a delineation logic 753, a perinodular zone logic 755, a feature extraction logic 757, a probability logic 758, and a classification logic 759. In one embodiment, the functionality associated with the set of logics 750 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 750 are implemented as ASICs or SOCs.

Image acquisition logic 751 acquires an image of a region of tissue. The image may be acquired from, for example, a CT apparatus. The region of tissue may be a section of tissue demonstrating cancerous pathology in a patient. The image of the region of tissue may include an image of a nodule. In one embodiment, the image is a 1 mm to 5 mm thick, no-contrast chest CT image with a pixel size of 0.7 mm center to center. Other imaging approaches may be used to generate and access the image accessed by image acquisition logic 751. Other image dimensions, pixel sizes, or resolutions may also be used. In one embodiment, the image is acquired from a DCE-MR imaging apparatus, and the region of tissue is a region of breast tissue demonstrating breast cancer pathology.

Delineation logic 753 automatically delineates the nodule by distinguishing nodule tissue within the image from the background of the image. In one embodiment, delineation logic 753 automatically delineates the nodule using SEG-vAC segmentation. In another embodiment, delineation logic 753 automatically delineates the nodule using threshold based segmentation, deformable boundary models, active-appearance models, active shape models, graph based models including Markov random fields (MRF), min-max cut approaches, or other image delineation approaches. In one embodiment, delineation logic 753 is configured to facilitate a human radiologist delineating the nodule. In one embodiment, delineation logic 753 segments tumor tissue from other, non-tumor tissue in an image of a breast demonstrating cancerous pathology. Delineation logic 753 may also segment breast wall tissue represented in the image. Delineation logic 753 may define a nodule boundary.

Perinodular zone logic 755 defines a perinodular zone based, at least in part, on the nodule tissue. In one embodiment, perinodular zone logic 755 defines the perinodular zone by defining a perinodular zone-plus-nodule region by dilating the nodule boundary a threshold amount, and subtracting the nodule region from the perinodular zone-plus-nodule region. In one embodiment, the threshold amount is within the range (4.9 mm, 7.0 mm). In another embodiment, perinodular zone logic 755 defines the perinodular zone using other ranges or techniques. For example, perinodular zone logic 755 may define the perinodular zone using a threshold amount within the range (3.5 mm, 5 mm) or the range (7 mm, 10 mm). In one embodiment, perinodular zone logic 755 may define the perinodular zone by subtracting the breast wall tissue from the image.

Feature extraction logic 757 extracts a set of features from the image. The set of features includes a first set of texture features, a set of shape features, or a second set of texture features. The first set of texture features or the set of shape features may be extracted from the nodule tissue in the image of the delineated nodule. The second set of texture features is extracted from the perinodular region. In one embodiment, the first set of texture features or the second set of texture features include a gray-level statistical feature, a steerable Gabor feature, a Haralick feature, a Law feature, a Law-Laplacian feature, an LBP feature, an inertia feature, a correlation feature, a difference entropy feature, a contrast inverse moment feature, a CoLIAGe feature, or a contrast variance feature. The set of shape features may include a location feature, a size feature, a perimeter feature, an eccentricity feature, an eccentricity standard deviation, a compactness feature, a roughness feature, an elongation feature, a convexity feature, an equivalent diameter feature, a radial distance feature, an area feature, or a sphericity feature. Feature extraction logic 757 may also select a subset of features from the set of features. Feature extraction logic 757 may select the subset of features based on, at least in part, a PCA-VIP ranking of the set of features. In one embodiment, feature extraction logic also extracts a set of tortuosity features from the image.

In one embodiment, feature extraction logic 757 extracts the set of features from a DCE-MR image during a first post-contrast phase, and during a second, peak-contrast phase. The first post-contrast phase may be the first scan collected following intravenous contrast agent injection. The second, peak-contrast phase may be a scan during which contrast enhancement intensity is the greatest, or during which contrast enhancement intensity is within a threshold level.

Probability logic 758 computes a probability that the nodule tissue is benign tissue. Probability logic 758 may compute the probability based, at least in part, on the subset of features. Probability logic 758 may also compute a probability that the nodule tissue will demonstrate a response to a treatment. In one embodiment, probability logic 758 computes a probability that a breast cancer nodule or tumor will achieve pCR after receiving NAC treatment.

Classification logic 759 classifies the nodule tissue based, at least in part, on the set of features or the probability. In one embodiment, classification logic 759 classifies the nodule as a benign Gr or a malignant carcinoma using an SVM classifier. The SVM classifier may be trained on a set of training features using a three-fold cross validation re-sampling approach. The set of training features may be selected using a PCA-VIP ranking of a set of features extracted from a set of training images. The set of training images may include a no-contrast CT image of a region of tissue demonstrating lung cancer pathology, or granuloma secondary to histoplasmosis infection. The set of training images may also include a DCE-MR image of a region of tissue demonstrating breast cancer pathology. In one embodiment, classification logic 759 classifies the nodule tissue as a carcinoma or a Gr using an LDA of the subset of features or using a QDA of the subset of features. In another embodiment, classification logic 759 may classify the nodule tissue using other analytical techniques.

In one embodiment, classification logic 759 classifies the nodule tissue as within a threshold probability of responding to NAC. Classification logic 759 bases the classification, at least in part, on the probability or the set of features. The set of features includes at least two features extracted from a DCE-MR image during the first post-contrast phase, and at least three features extracted from the DCE-MR image during the second, peak-contrast phase. The at least two features and the at least three features may be selected from the set of features using a feed forward feature selection approach.

In another embodiment, classification logic 759 may control a CADx system to classify the image based, at least in part, on the classification. For example, classification logic 759 may control a lung cancer CADx system to classify the image based, at least in part, on the set of features. In other embodiments, other types of CADx systems may be controlled, including CADx systems for distinguishing nodules among breast cancer, oral cancer, prostate cancer, colon cancer, brain cancer, and other diseases where disease classification and prognosis prediction may be based on textural or shape features quantified from CT images of a nodule or DCE-MR images of a region of tissue demonstrating cancerous pathology.

In one embodiment of apparatus 700, the set of logics 750 also includes a tortuosity logic. The tortuosity logic identifies a vessel associated with the nodule. The tortuosity logic identifies the centerline and a branching point of the vessel associated with the nodule. The tortuosity logic computes a torsion for the segment of the vessel. The tortuosity logic also computes a curvature of a voxel of a vessel segment, where the curvature is proportional to the inverse of an osculating circle's radius. The tortuosity logic extracts a set of tortuosity features from the image. The set of tortuosity features may include the mean of torsion of a vessel segment, or the standard deviation of torsion of a vessel segment. The set of tortuosity features also may include the mean and standard deviation of the mean curvature of a group of vessel segments. The set of tortuosity features also may include the mean and standard deviation of the standard deviation of a vessel segment curvature and a total vessel segment length. The set of tortuosity features may also include branching statistics associated with the vessel. The tortuosity logic also selects a subset of tortuosity features from the set of tortuosity features based, at least in part, on a PCA or PCA-VIP of the set of tortuosity features. The subset of tortuosity features may include at least three tortuosity features. In one embodiment, the classification logic 759 classifies the nodule tissue based, at least in part, on the set of features, where the set of features includes the first set of texture features, the second set of texture features, the set of shape features, and the set of tortuosity features.

In one embodiment of apparatus 700, the set of logics 750 also includes a display logic. The display logic may control the CADx system to display the classification, the nodule, the perinodular zone, the texture features, the tortuosity features, or the shape features, on a computer monitor, a smartphone display, a tablet display, or other displays. Displaying the classification or the features may also include printing the classification or the features. The display logic may also control the CADx to display an image of the region of tissue demonstrating a nodule. The image of the region of tissue demonstrating a nodule may include a delineated or segmented representation of the nodule. By displaying the features and the image of the nodule, example apparatus provide a timely and intuitive way for a human pathologist to more accurately classify pathologies demonstrated by a patient, thus improving on conventional approaches to predicting cancer recurrence and disease progression.

Figure 8:
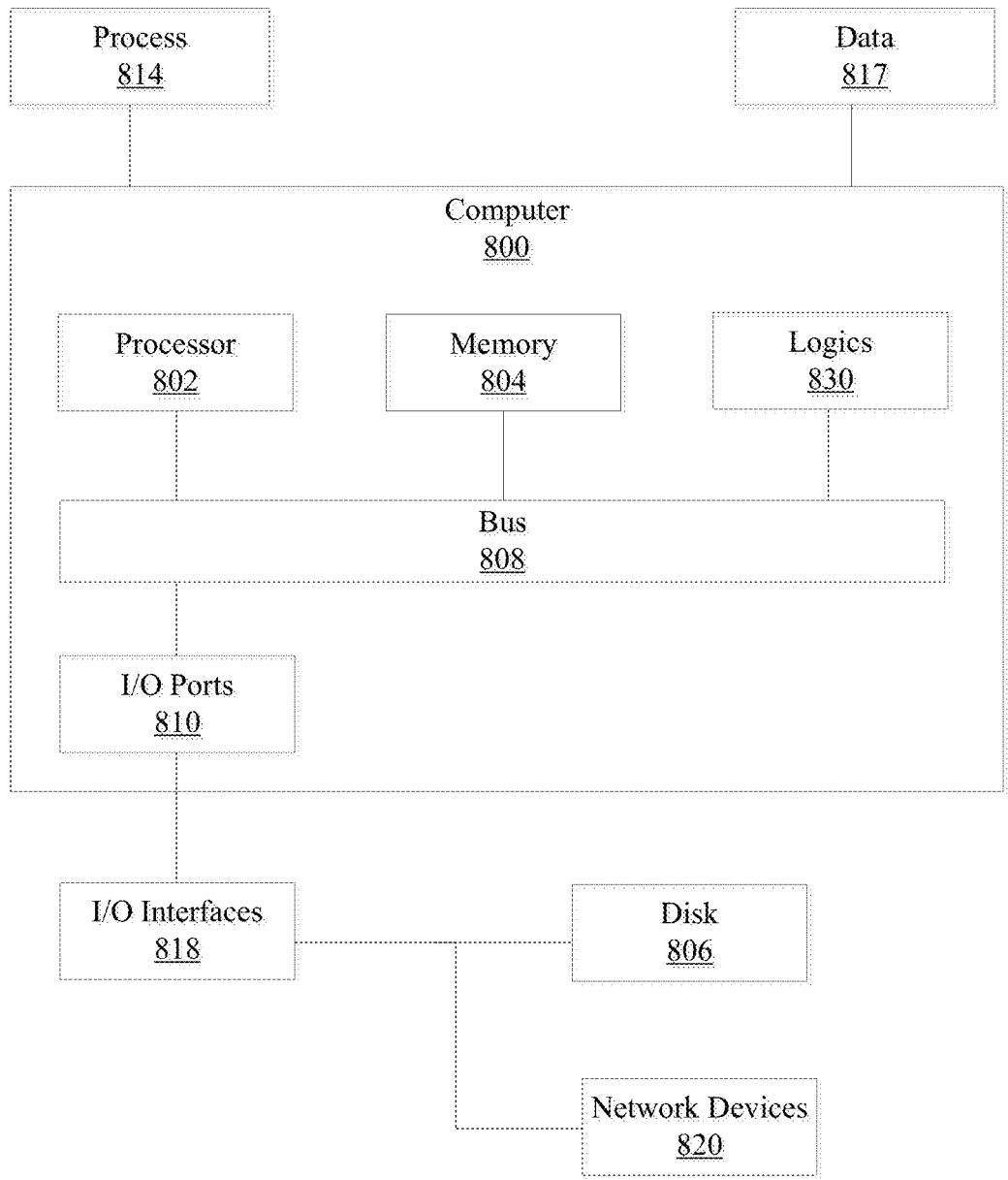
FIG. 8 illustrates an example computer in which example methods and apparatus may operate.

FIG. 8 illustrates an example computer 800 in which example methods illustrated herein can operate and in which example circuits or logics may be implemented. In different examples, computer 800 may be part of a CT system or MRI system, may be operably connectable to a CT system or MRI system, or may be part of a CADx system.

Computer 800 includes a processor 802, a memory 804, and input/output ports 810 operably connected by a bus 808. In one example, computer 800 may include a set of logics 830 that perform a method of characterizing a nodule in a region of lung tissue. Thus, the set of logics 830, whether implemented in computer 800 as hardware, firmware, software, and/or a combination thereof may provide means (e.g., hardware, software) for characterizing a nodule in a region of lung tissue. In different examples, the set of logics 830 may be permanently and/or removably attached to computer 800. In one embodiment, the functionality associated with the set of logics 830 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 830 are implemented as ASICs or SOCs.

Processor 802 can be a variety of various processors including dual microprocessor and other multi-processor architectures. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a solid state device (SSD), a flash memory card, or a memory stick. Furthermore, disk 806 may include optical drives like a CD-ROM or a digital video ROM drive (DVD ROM). Memory 804 can store processes 814 or data 817, for example. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, logics, and peripherals using other busses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, digital whole slide scanners, a CT machine, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, a data storage device, and other media from which a computer, a processor or other electronic device can read.

"Logic", as used herein, includes but is not limited to hardware, firmware, software in execution on a machine, or combinations of each to perform a function(s) or an action(s), or to cause a function or action from another circuit, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logics into one physical logic or circuit. Similarly, where a single logical logic is described, it may be possible to distribute that single logic between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing instructions that when executed by a processor control the processor to perform operations, the operations including:
    accessing a radiological image of a region of tissue demonstrating lung nodules;
    segmenting a nodule in the image from the background of the image by automatically distinguishing nodule tissue in the image from the background of the image using a spectral embedding gradient vector flow active contour (SEGvAC) approach, the SEGvAC approach comprising:
        generating an initial lung mask by separating a lung region represented in the image from surrounding lung anatomy;
        generating a refined image by removing a non-granuloma structure from the initial lung mask using a rule-based classifier;
        generating a spectral embedding (SE) representation by projecting at least one refined image into a three dimensional (3D) SE space; and
        extracting a nodule boundary from the SE representation;
    defining a perinodular region by:
        segmenting a breast wall from the image;
        removing the breast wall from the image;
        generating an outer perinodular boundary by dilating the nodule boundary a threshold amount;
        generating a perinodular region by subtracting the nodule from the region defined by the outer perinodular boundary;
    selecting a first set of texture features from the perinodular region;
    selecting a second set of texture features or a set of shape features from the nodule;
    computing a probability that the nodule is benign based, at least in part, on the first set of texture features, the second set of texture features, or the set of shape features; and
    providing a prognosis prediction based on the probability.

2. The non-transitory computer-readable storage device of claim 1, where the rule-based classifier selects the non-granuloma structure to remove from the initial lung mask based on a convexity measure of the non-granuloma structure, or an elongation measure of the non-granuloma structure.

3. The non-transitory computer-readable storage device of claim 1 where extracting a nodule boundary from the SE representation includes extracting the nodule boundary using a gradient vector flow field (GVF) active contour model.

4. The non-transitory computer-readable storage device of claim 3, where the GVF force drives the active contour.

5. A non-transitory computer-readable storage device storing computer executable instructions that when executed by a computer control the computer to perform a method, the method comprising:
    acquiring an image of a region of tissue demonstrating cancerous pathology;
    distinguishing nodule tissue represented in the image from the background of the image by defining a nodule boundary using a spectral embedding gradient vector flow active contour (SEGvAC) approach;
    defining a perinodular zone by:
        segmenting a breast wall from the image;
        removing the breast wall from the image;
        generating an outer perinodular boundary by dilating the nodule boundary a threshold amount;
        generating a perinodular region by subtracting the nodule from the region defined by the outer perinodular boundary;
    extracting a set of features from the image, where the set of features comprises a first set of texture features extracted from the nodule tissue in the image or a set of shape features extracted from the nodule tissue in the image, and a second set of texture features extracted from the perinodular region;
    selecting a subset of features from the set of features based on, at least in part, a principal component analysis (PCA) variable importance on projections (VIP) ranking of the set of features;
    computing a probability that the nodule tissue is benign tissue, or that the nodule tissue will demonstrate a response to a treatment based, at least in part, on the subset of features; and
    classifying the nodule tissue based, at least in part, on the probability, and at least one of the image, the set of features, or the subset of features.

6. The non-transitory computer-readable storage device of claim 5, where the first set of texture features or the second set of texture features includes a gray-level statistical feature, a steerable Gabor feature, a Haralick feature, a Law feature, a Law-Laplacian feature, a gradient feature, a local binary pattern (LBP) feature, an inertia feature, a correlation feature, a difference entropy feature, a contrast inverse moment feature, a co-occurrence of local anisotropic gradient orientations (CoLIAGe) feature, or a contrast variance feature.

7. The non-transitory computer-readable storage device of claim 6, where the set of shape features includes a size feature, an area feature, a perimeter feature, an eccentricity feature, an extend feature, a compactness feature, a radial distance feature, a roughness feature, an elongation feature, a convexity feature, an equivalent diameter feature, or a sphericity feature.

8. The non-transitory computer-readable storage device of claim 5, where the image is a no-contrast computed tomography image of a region of tissue demonstrating lung cancer pathology, or where the image is a dynamic contrast enhanced (DCE) magnetic resonance (MR) image of a region of tissue demonstrating breast cancer pathology.

9. The non-transitory computer-readable storage device of claim 5 where computing the probability that the nodule tissue will demonstrate a response to a treatment includes computing the probability that the nodule will achieve pathological complete response (pCR) to neo-adjuvant chemotherapy (NAC).

10. The non-transitory computer-readable storage device of claim 5, where computing the probability includes:
    providing the subset of features to a support vector machine (SVM) classifier, where the SVM classifier is trained on a set of training features using a three-fold cross-validation re-sampling approach, and where the set of training features is selected using a PCA-VIP ranking of a set of features extracted from a set of training images, where the SVM classifier computes the probability based, at least in part, on the subset of features; and
    receiving the probability from the SVM classifier.

11. The non-transitory computer-readable storage device of claim 5, where classifying the nodule tissue includes classifying the nodule tissue as within a threshold probability of responding to neo-adjuvant chemotherapy (NAC) based on the probability or the set of features, where the set of features includes at least two features extracted during a first post-contrast phase, and at least three features extracted during a second, peak-contrast phase.

12. A non-transitory computer-readable storage device storing instructions that when executed by a processor control the processor to perform operations, the operations including:
    accessing an image of a region of tissue demonstrating cancerous pathology;
    segmenting a nodule represented in the image by extracting a nodule boundary from the image by automatically distinguishing nodule tissue in the image from the background of the image using a spectral embedding gradient vector flow active contour (SEGvAC) approach;
    defining a perinodular region in the image by:
        segmenting a breast wall from the image;
        removing the breast wall from the image;
        generating an outer perinodular boundary by dilating the nodule boundary a threshold amount;
        generating a perinodular region by subtracting the nodule from the region defined by the outer perinodular boundary;
    generating a set of perinodular texture features based on the perinodular region;
    computing a probability that the nodule is benign based, at least in part, on the set of perinodular texture features; and
    controlling a computer aided diagnosis (CADx) system to generate a classification of the nodule based, at least in part, on the set of perinodular texture features, or the probability that the nodule is benign.

13. The non-transitory computer-readable storage device of claim 12, where accessing the image of the region of tissue comprises accessing a computed tomography (CT) image of a region of lung tissue, where the CT image is a no-contrast chest CT image.

14. The non-transitory computer-readable storage device of claim 12, the SEGvAC approach comprising:
    generating an initial lung mask by separating a lung region represented in the image from surrounding lung anatomy;

generating a refined image by removing a non-granuloma structure from the initial lung mask using a rule-based classifier, where the rule-based classifier selects the non-granuloma structure to remove from the initial lung mask based on a convexity measure of the non-granuloma structure, or an elongation measure of the non-granuloma structure;

generating a spectral embedding (SE) representation by projecting at least one refined image into a three dimensional (3D) SE space; and extracting a nodule boundary from the SE representation using a gradient vector flow field (GVF) active contour model, where a GVF force drives the active contour.

15. The non-transitory computer-readable storage device of claim 12, where generating the set of perinodular texture features comprises:

extracting a first set of texture features from the perinodular region; and reducing the first set of texture features using principal component analysis (PCA) variable importance on projections (VIP) feature ranking.

16. The non-transitory computer-readable storage device of claim 12, the operations further including:

extracting a set of nodule features from the nodule, where the set of nodule features comprises a set of shape features or a second set of texture features; and generating a reduced set of nodule features by reducing the set of nodule features using principal component analysis (PCA) variable importance on projections (VIP) feature ranking.

17. The non-transitory computer-readable storage device of claim 12, where accessing the image of the region of tissue includes accessing a dynamic contrast-enhanced (DCE) magnetic resonance imaging (MRI) image of a region of breast tissue.

18. The non-transitory computer-readable storage device of claim 12, the operations further including:

computing a probability that the nodule will achieve pathological complete response (pCR) based, at least in part, on the set of perinodular texture features; and controlling the CADx system to generate a classification of the nodule based, at least in part, on the set of perinodular texture features, or the probability that the nodule will achieve pCR.

* * * * *